(12) United States Patent
Uchida

(10) Patent No.: US 6,409,343 B1
(45) Date of Patent: Jun. 25, 2002

(54) OPHTHALMIC APPARATUS

(75) Inventor: Koji Uchida, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/412,498

(22) Filed: Oct. 5, 1999

(30) Foreign Application Priority Data

Oct. 8, 1998 (JP) .......................................... 10-300337

(51) Int. Cl.[7] .................................................. A61B 3/14
(52) U.S. Cl. ..................................................... 351/208
(58) Field of Search ................................ 351/205, 206, 351/208, 209, 211, 212, 221, 246

(56) References Cited

U.S. PATENT DOCUMENTS 5,910,833 A * 6/1999 Iijima .......................... 351/208
5,975,698 A * 11/1999 Iijima .......................... 351/208

* cited by examiner

*Primary Examiner*—George Manuel
(74) *Attorney, Agent, or Firm*—Robin, Blecker & Daley

(57) ABSTRACT

Disclosed is an ophthalmic apparatus having a measurement unit for measuring an eye to be examined, an illumination light source, disposed near the measurement unit, for illuminating the eye, an area sensor for picking up an image of the anterior part of the eye illuminated by the illumination light source, a driver for driving the measurement unit relative to the eye forward or backward, and a determining unit for determining whether signal levels throughout the whole area of the area sensor are not more than a predetermined level. When the determining unit determines that the signal levels are not more than the predetermined level, it is judged that the apparatus is too close to the eye and the driver drives the measurement unit away from the anterior part of the eye.

14 Claims, 14 Drawing Sheets

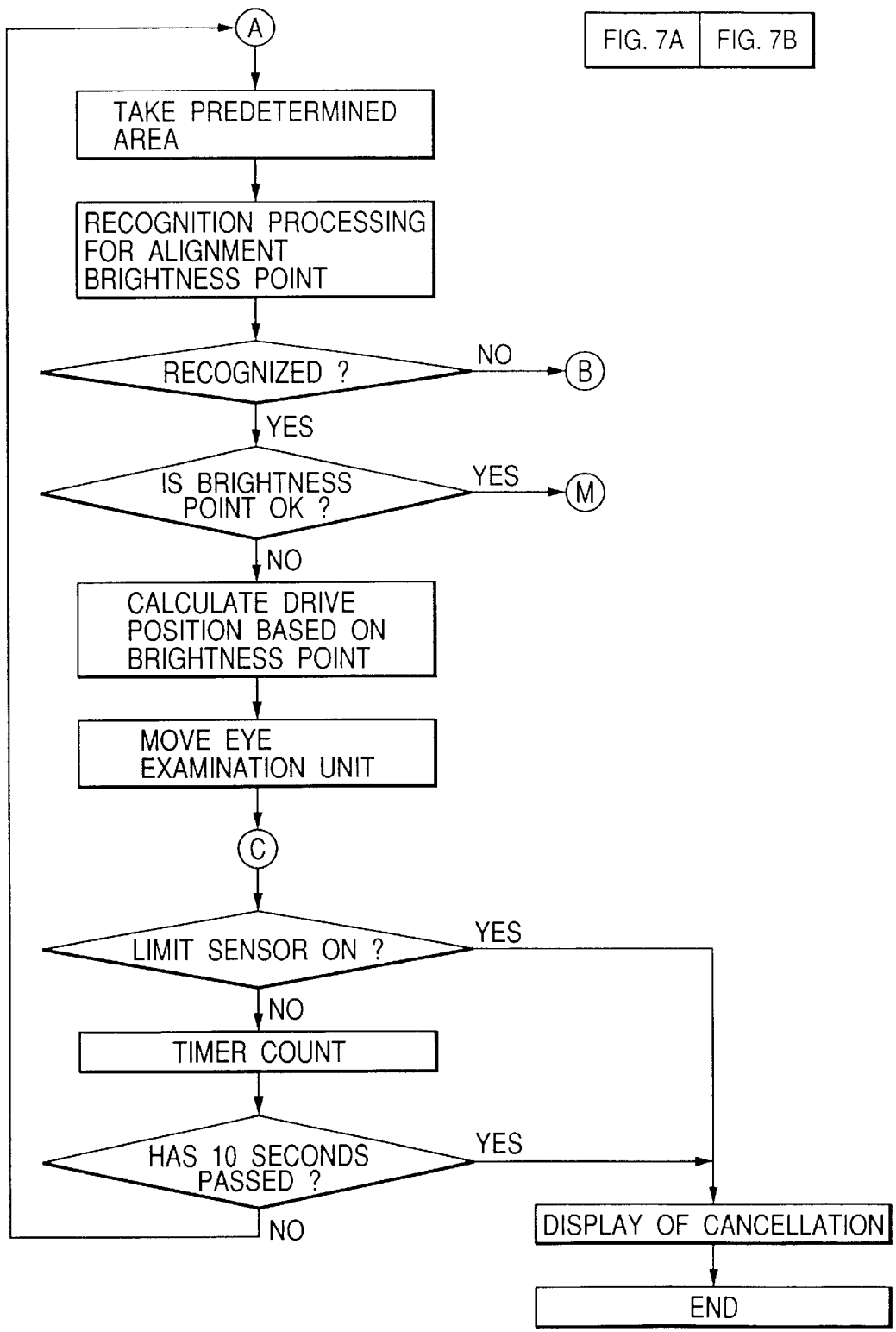

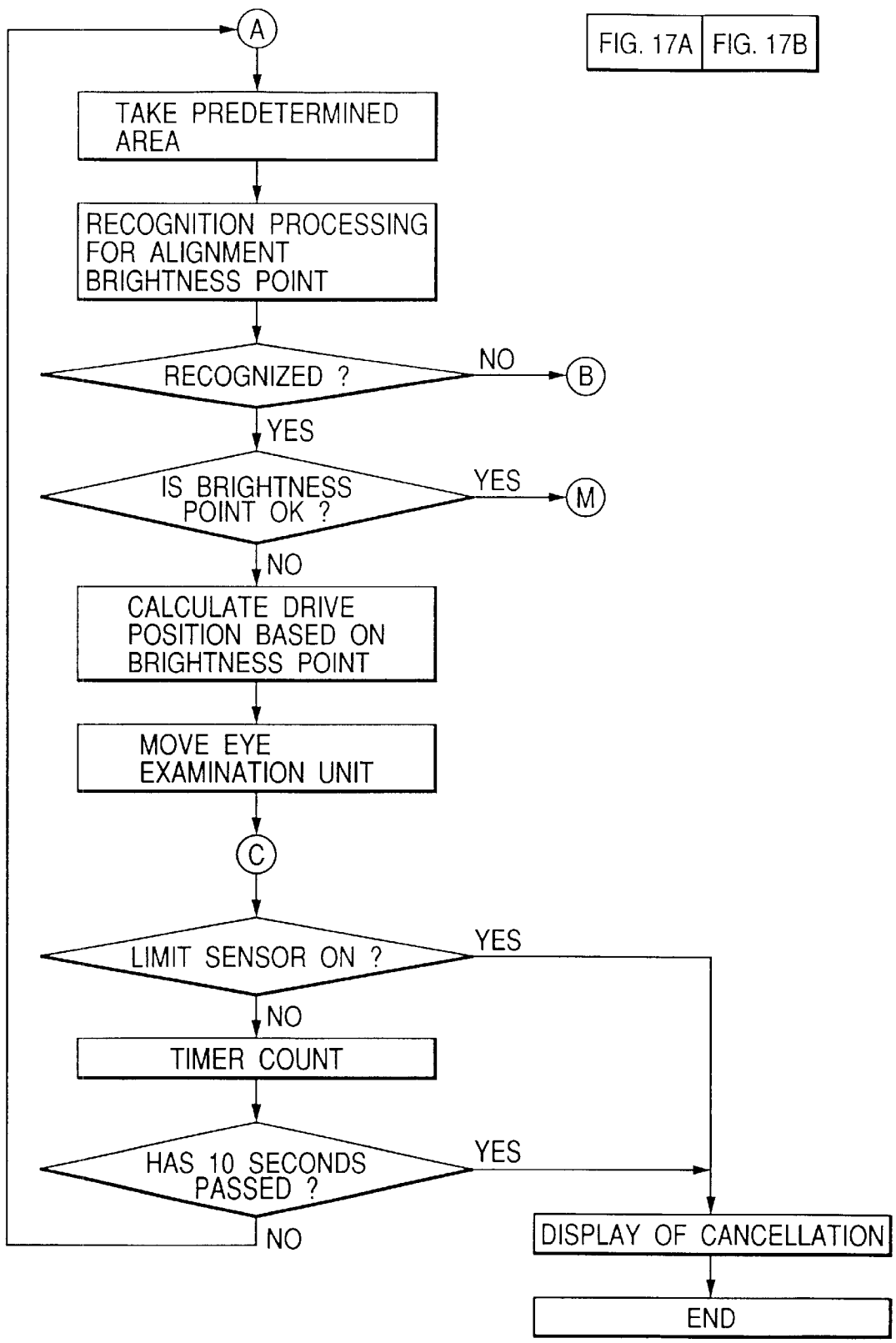

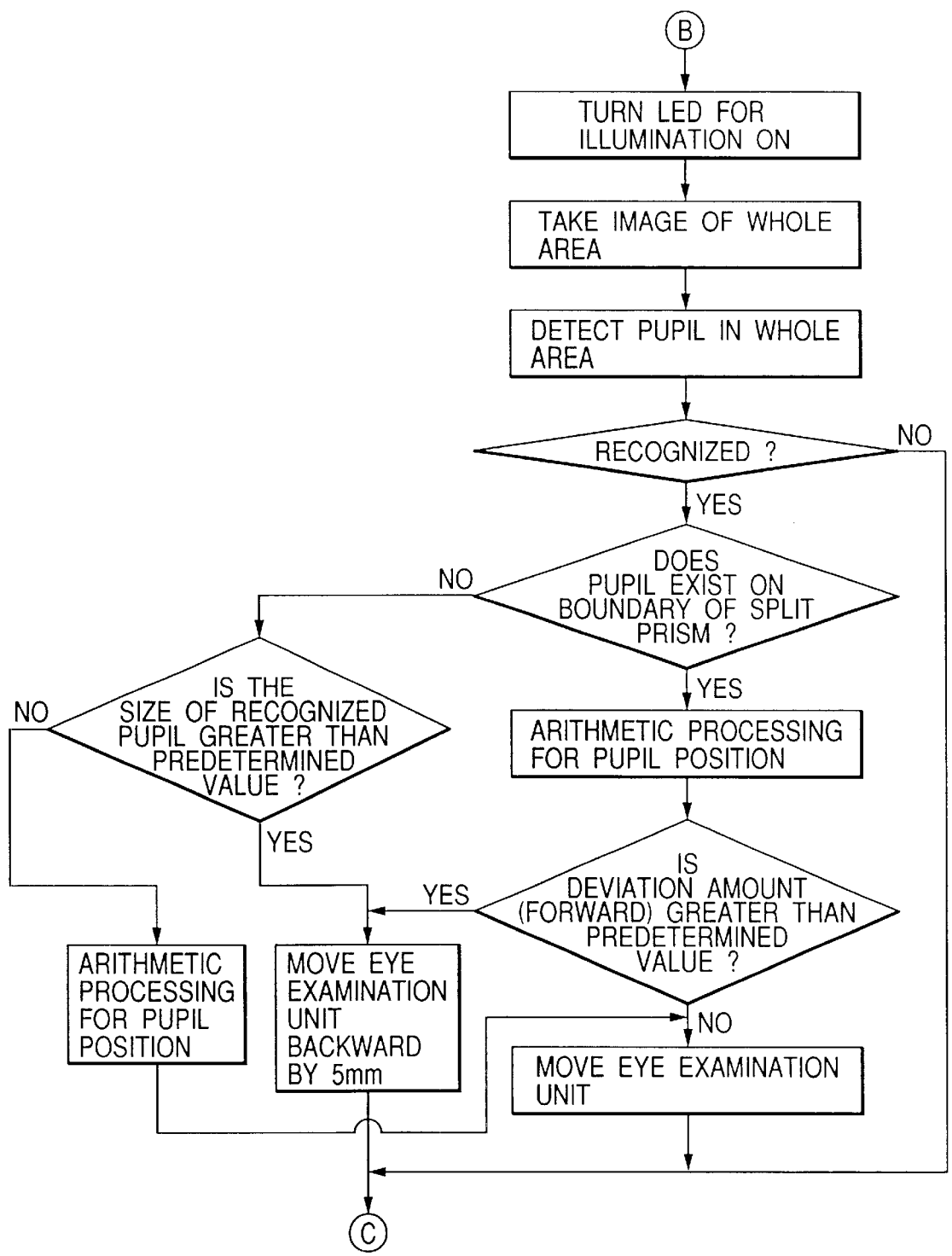

OPHTHALMIC APPARATUS

BACKGROUND OF THE INVENTION

1. Field of the Invention

The present invention relates to an ophthalmic apparatus used for ophthalmoscopy and tonometry at ophthalmic hospitals and the like.

2. Related Background Art

The ophthalmic apparatus conventionally known includes the ophthalmic apparatus arranged to carry out automatic alignment by projecting an alignment beam toward the cornea and receiving reflected light thereof, which is disclosed in Japanese Patent Application Laid-Open No. 62-19150, the ophthalmic apparatus arranged to perform such control as to retract an eye examination unit when the eye examination unit is too close to an eye to be examined, using an alignment optical system and a measurement optical system for positioning between the eye to be examined and the apparatus, an apparatus arranged to carry out anti-proximity control of the eye examination unit by use of an ultrasonic sensor or a capacitance sensor placed on the eye side of the eye examination unit, an apparatus with a driving unit preliminarily so limited as to prevent the eye examination unit from approaching the eye over a predetermined distance, and so on.

In the above-stated prior art examples, however, where the automatic alignment and anti-proximity is carried out by use of the alignment optical system, a light receiving unit cannot receive the cornea-reflected light unless the examination unit is preliminarily positioned to some extent vertically and laterally with respect to the eye to be examined; the detection range of the automatic alignment and anti-proximity becomes narrower thereby. When the ultrasonic sensor or the capacitance sensor is used, the structure becomes complicated because of increase of components including those for mounting of these sensors, a driving circuit, a detection circuit, and so on. When the driving unit is limited to the predetermined position, there arises a problem that the eye to be detected cannot be detected if the eye suddenly approaches the apparatus immediately before eye examination.

SUMMARY OF THE INVENTION

An object of the present invention is to provide an ophthalmic apparatus of safe and simple structure capable of widening the detection range of automatic alignment and carrying out the anti-proximity in a wide range, overcoming the above problems.

An ophthalmic apparatus of the present invention is an ophthalmic apparatus comprising:

a measurement unit for measuring an eye to be examined;

an illumination light source disposed near the measurement unit, for illuminating the eye;

an area sensor for picking up an image of the eye illuminated by said illumination light source;

driving means for driving said measurement unit relative to the eye forward or backward;

determining means for determining whether signal levels throughout an entire area of said area sensor are not more than a predetermined level; and control means for controlling said driving means so as to drive the measurement unit away from said eye, when said determining means determines that the signal levels are not more than the predetermined level.

Another ophthalmic apparatus of the present invention is an ophthalmic apparatus comprising:

a measurement unit for measuring an eye to be examined;

an illumination light source disposed near the measurement unit, for illuminating the eye;

an area sensor for picking up an image of the anterior part of the eye illuminated by said illumination light source;

an optical unit for optically splitting the image of the anterior part of the eye and for projecting the images of the anterior part of the eye thus split onto said area sensor;

driving means for driving said measurement unit relative to the eye forward or backward;

detecting means for detecting a deviation amount between the images of the pupil split by said optical unit, based on an output of said area sensor; and control means for controlling said driving means so as to drive the measurement unit away from said eye, based on the result of detection by said detecting means.

Still another ophthalmic apparatus of the present invention is an ophthalmic apparatus comprising:

a measurement unit for measuring an eye to be examined;

an illumination light source disposed near the measurement unit, for illuminating the eye;

an area sensor for picking up an image of the anterior part of the eye illuminated by said illumination light source;

driving means for driving said measurement unit relative to the eye forward or backward;

determining means for determining a size of the pupil of the eye, based on an output of said area sensor; and control means for controlling said driving means so as to drive the measurement unit away from said eye, based on the result of determination by said determining means.

BRIEF DESCRIPTION OF THE DRAWINGS

FIG. 17 is comprised of FIGS. 17A and 17B showing flowcharts of the second embodiment;

DETAILED DESCRIPTION OF THE PREFERRED EMBODIMENTS

The present invention will be described in detail on the basis of the embodiments illustrated.

Figure 1:
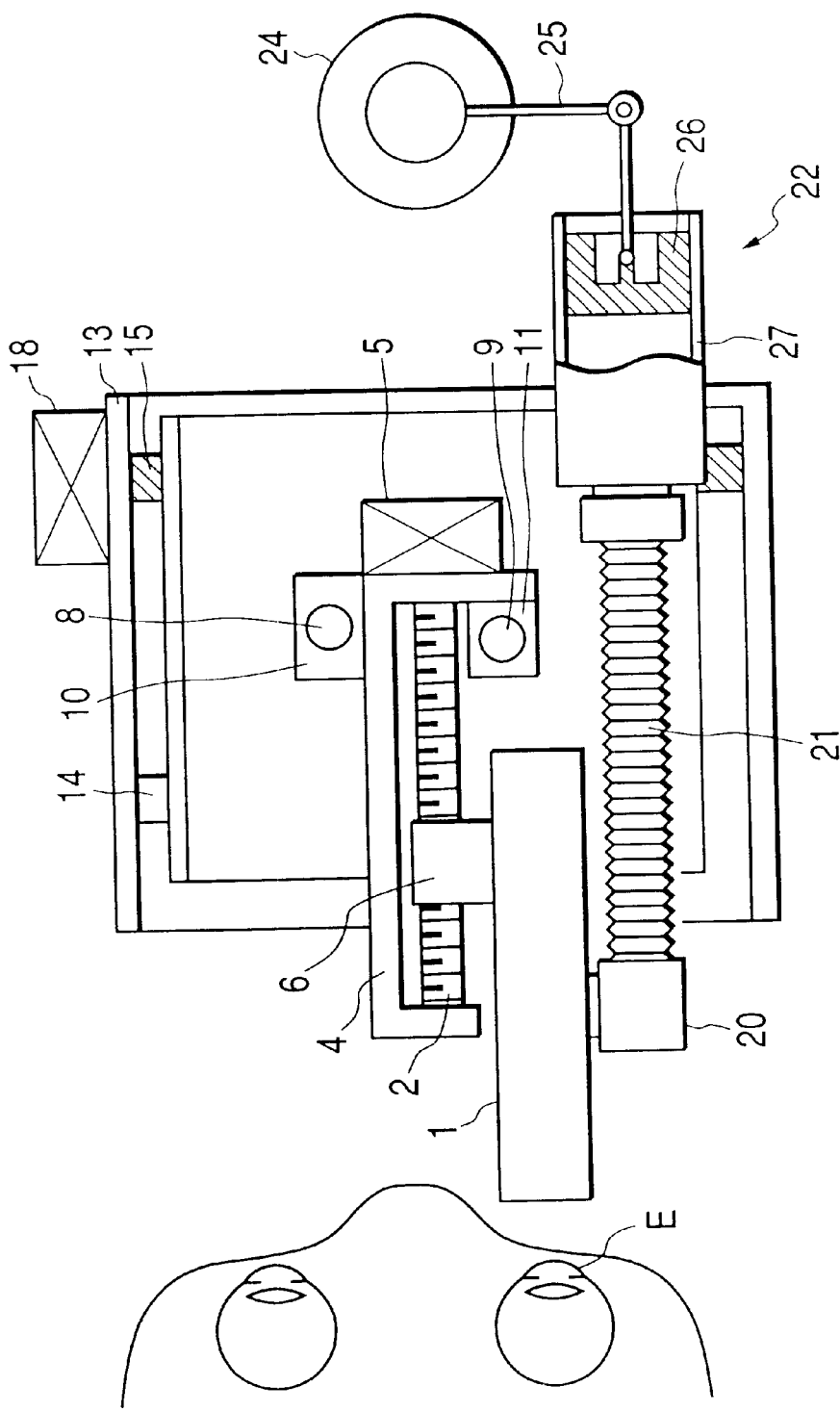
FIG. 1 is a plan view of the first embodiment.
Figure 2:
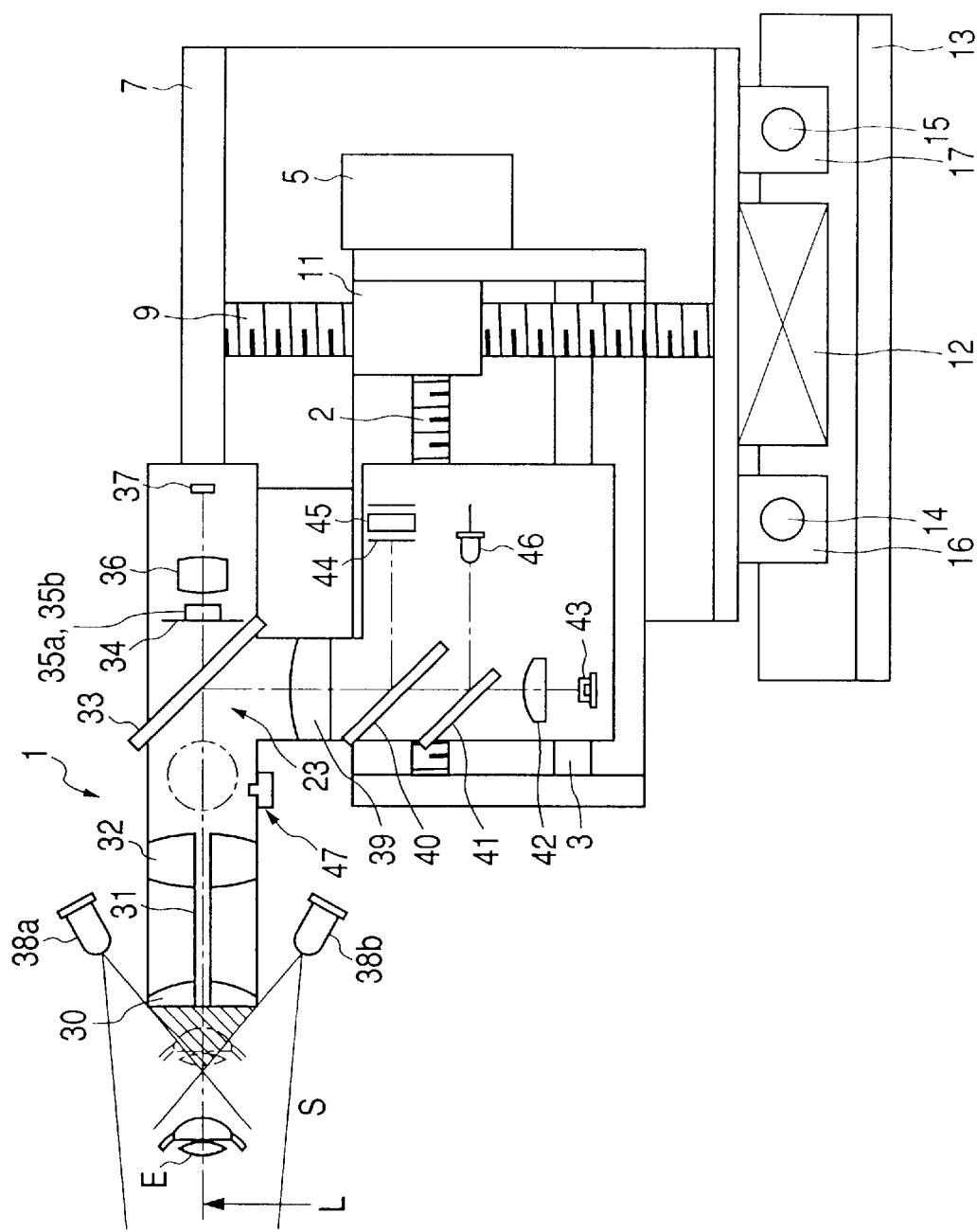
FIG. 2 is a side view.

FIG. 1 is a plan view of an auto-alignment tonometer of the first embodiment and FIG. 2 is a side view thereof. A tonometry unit 1 is supported on a frame 4 for moving the tonometry unit 1 forward and backward, by feed screw 2 and guide shaft 3. A motor 5 for driving of the forward and backward (lengthwise) motion is directly connected to one end of the feed screw 2 on the frame 4 and an internal thread bearing 6 in mesh with the feed screw 2 is fixed to the side surface of the tonometry unit 1. The feed screw 2 rotates with rotational driving of the lengthwise motion motor 5, whereupon the tonometry unit 1 can be moved back and forth along the guide shaft 3.

A guide shaft 8 and a feed screw 9 are fixed vertically to a frame 7 for moving the tonometry unit 1 and the frame 4 up and down, and vertical movement can be effected by moving the frame 4 for the lengthwise motion together with the tonometry unit 1 up and down relative to the frame 7. A bearing 10 of the guide shaft 8 and an internal thread bearing 11 of the feed screw 9 are fixed to the frame 4 and a motor 12 for driving the feed screw 9 in order to move the frame 4 up and down is attached to the lower part of the frame 7.

For moving the tonometry unit 1 left and right in a similar fashion to the vertical motion, a guide shaft 14 and a feed screw 15 are arranged horizontally in a frame 13 (base) for lateral (crosswise) motion, whereby the frame 7, together with the tonometry unit 1 and the frame 4, can be moved horizontally relative to the frame 13. A bearing 16 of the guide shaft 14 and an internal thread bearing 17 of the feed screw 15 are fixed to the lower part of the frame 7 and a motor 18 for driving the feed screw 15 in the crosswise motion as a driving source is attached to the side surface of the frame 13 for the crosswise motion.

A joint 20 as an air inlet is fixed to the side surface of the tonometry unit 1, and a flexible tube 21 and an airflow generator 22 are connected to another port of the joint 20. The airflow generator 22 is fixed to the frame 7 for vertical movement, whereby the airflow generator 22, together with the tonometry unit 1, can be moved left and right. The airflow generator 22 is not linked with the vertical and lengthwise motions of the tonometry unit 1 and always feeds constant air into an air chamber 23 in the entire stroke ranges of the vertical and lengthwise motions because of freedom of the flexible tube 21. The airflow generator 22 is composed of a rotary solenoid 24, a link mechanism 25, a piston 26, and a cylinder 27 and is arranged to feed the air in the cylinder 27 into the tonometry unit 1 by horizontally moving the piston 26 with rotation of the rotary solenoid 24.

Figure 3:
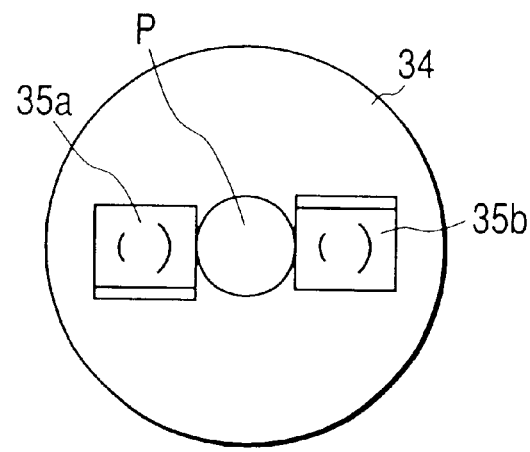
FIG. 3 is a front view of a mask.

Inside the tonometry unit 1, an eye viewing optical system is placed on the optical axis L in the opposed relation to the eye E to be examined. The eye viewing optical system has a lens 30, a nozzle 31, a lens 32, a dichroic mirror 33, a mask 34, two splitting prisms 35a, 35b, a lens 36, and an image pickup element 37 arranged in the stated order from the side of the eye E and LED light sources 38a, 38b for illuminating the anterior part of the eye are located near and beside the lens 30 above and below. FIG. 3 is a view of the mask 34 and the splitting prisms 35a, 35b from the optical-axis direction.

An aperture P in the central part of the mask is provided for transmitting light reflected by the anterior part out of the light from the light sources 38a, 38b. Further, the prisms 35a, 35b have such an optical property as to transmit only the wavelength of a light source 43.

In the alignment optical system, a light-receiving optical system thereof is shared in part with the eye viewing optical system and along the direction of incidence of the dichroic mirror 33 there are a lens 39, a half mirror 40, a dichroic mirror 41, a projection lens 42, and a light source 43 arranged in the stated order, thus forming a projection optical system. Along the direction of reflection of the half mirror 40, an aperture 44 and a light receiving element 45 are arranged to form a corneal deformation detecting optical system. A LED light source 46 for fixed sight as a visible light source is placed in the direction of incidence of the dichroic mirror 41 to form a fixation target projecting optical system. A pressure sensor 47 for detecting internal pressure inside the air chamber 23 is attached to the air chamber 23.

In the above structure, an observed image of the eye E illuminated by the LED light sources 38a, 38b for illumination of the anterior part, which emit the infrared light, is guided through the lens 30, the outside of the nozzle 31, and the lens 32 and is then transmitted by the dichroic mirror 33 to be guided through the mask 34 and lens 36 to the image pickup element 37. The LED light sources 38a, 38b are arranged so that the front part of the tonometry unit 1 makes a shadow; therefore, the eye will go into this shadow if the eye moves into close proximity of the tonometry unit 1. It is thus determined that the eye is too close when the whole eye becomes dark, as described hereinafter. On the other hand, in the alignment projection optical system, the light emitted from the light source 43 travels through the projection lens 42, the dichroic mirror 41, and the half mirror 40 and then through the lens 39, and part of the light is reflected by the dichroic mirror 33 to be directed toward the eye E through the inside of the nozzle 31.

The light reflected by the cornea of the eye E travels through the lens 30 and lens 32 and part of the light is transmitted by the dichroic mirror 33 to travel via the mask 34 to the separating prisms 35a, 35b. The light is separated into two beams by the separating prisms 35a, 35b to be guided through the lens 36 to the image pickup element 37. In the eye viewing optical system, the light travels through the center aperture P of the mask 34 to form an image on the image pickup element 37; in the alignment light-receiving optical system only the light of the wavelength of the light source 43 reaches the prisms 35a, 35b, the light is refracted upward by the left prism 35a while the light is refracted downward by the right prism 35b. At an appropriate working distance, spot images of the light source 43 are formed as two brightness points aligned on a vertical line near the center on the image pickup element 37.

Figure 4:
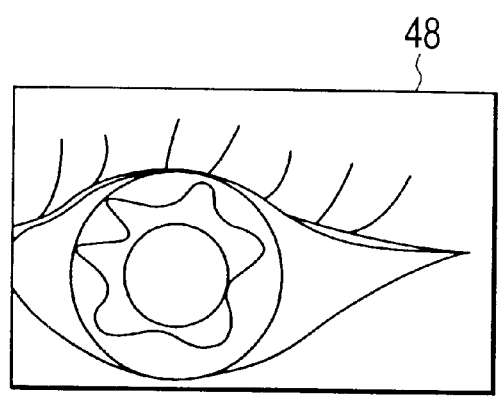
FIG. 4 is an explanatory diagram of an observed image.

FIG. 4 is an explanatory diagram of an observed image. The image formed on the image pickup element 37 is displayed on a display 48. With a lengthwise shift of the working distance, the two brightness points move relative to each other left and right from the reference position at the appropriate working distance. If the tonometry unit 1 moves up and down and left and right with respect to the eye E to be examined, the two brightness points will also move up and down and left and right according to the amount of the shift without changing their relative positions. FIG. 4 shows a state in which the eye E to be examined deviates a little left and down and the working distance also deviates slightly.

The projection optical system for detection of corneal deformation has the common structure to the alignment projection optical system, and the light emitted from the light source 43 travels through the projection lens 42, the dichroic mirror 41, and the half mirror 40 and then through the lens 39 to be reflected by the dichroic mirror 33 to be directed through the inside of the nozzle 31 toward the eye E. In the light-receiving optical system the cornea-reflected light from the deformed cornea travels through the lens 30 and lens 32 and part of the light is reflected by the dichroic mirror 33 to travel through the lens 39 to the half mirror 40. Part of the light is reflected by the half mirror 40 to be guided through the aperture 44 to the light receiving element 45. The light receiving element is located at a position at which it outputs a maximum output when the cornea becomes applanate. Therefore, the applanate state of the cornea is detected when a computer (not illustrated) detects the maximum output of the light receiving element.

In the fixation target projection optical system, the visible light emitted from the LED light source 46 for fixed sight is reflected by the dichroic mirror 41 and transmitted by the half mirror 40, travels through the lens 39 to be reflected by the dichroic mirror 33, and is guided through the inside of the nozzle 31 to the eye E to be examined.

Figure 5:
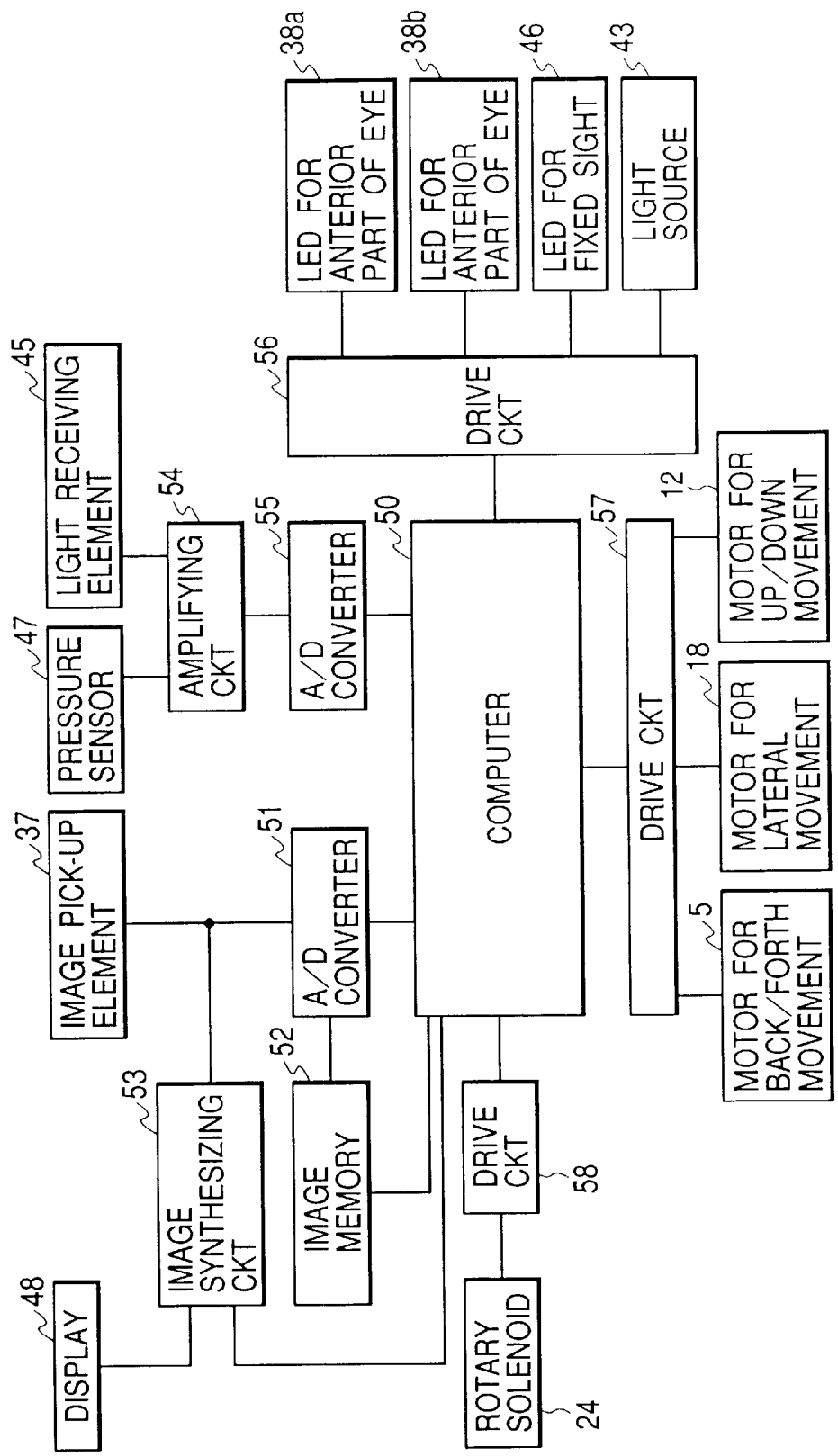
FIG. 5 is a block circuit structural diagram of an electric control unit.

FIG. 5 is a block circuit structural diagram of an electric control unit, which is provided with a computer 50 for carrying out the total control. An output of the image pickup element 37 is connected via A/D converter 51 to the computer 50 and to an image memory 52, and an output of the image memory 52 is connected to the computer 50. Further, an output of the image pickup element 37 is also connected via an image synthesizing circuit 53 to the display 48 and an output of the image synthesizing circuit 53 is connected to the computer 50. Outputs of the light receiving element 45 and pressure sensor 47 are connected via an amplifying circuit 54 and an A/D converter 55 to the computer 50.

On the other hand, an output of the computer 50 is connected via a driving circuit 56 to each of the anterior illuminating LED light sources 38a, 38b, the light source 43, and the fixed sight LED light source 46. The computer is also connected via a driving circuit 57 to each of the lengthwise motion motor 5, the vertical motion motor 12, and the crosswise motion motor 18, and the computer is further connected via a driving circuit 58 to the rotary solenoid 24.

In this structure, the eye viewing light and the alignment light are received by the image pickup element 37 to be subjected to photoelectric conversion and a signal therefrom is sent via the image synthesizing circuit 53 to the display 48. At this time, in order to display the tonometry result and the alignment target, the image synthesizing circuit 53 accepts a character synthesis signal from the computer 50, combines it with the observed image, and displays a synthesized image on the display 48. The observed image to be subjected to alignment detection processing is sent via the A/D converter 51 for digitizing an image, to the image memory 52 and the image stored in the image memory 52 is read into the computer 50 to be subjected to processes for detection of pupil position and for detection of alignment position.

The amplifier 54 amplifies the signal of the pressure sensor 47 for detecting the pressure inside the air chamber 23 and the signal resulting from the photoelectric conversion in the light receiving element 45 as a photoreceptive unit of the corneal deformation detecting optical system and the A/D converter 55 digitize the signals to send digital signals to the computer 50. A control signal is sent from the computer 50 to the driving circuit 56 to control on/off or the light amounts of the anterior illuminating LED light sources 38a, 38b, the light source 43, and the fixed sight LED light source 46.

A control signal from the computer 50 is sent to the motor driving circuit 57 in accordance with a positional deviation between the eye E and the tonometry unit 1 to control the rotating direction and driving speed of the lengthwise motion motor 5, the vertical motion motor 12, and/or the crosswise motion motor 18. Each of these motors 5, 12, 18 can also be driven by manipulating a track ball or a mouse or by input through a keyboard, if the eye E to be examined cannot be detected by the viewing optical system or the alignment optical system. When the appropriate alignment state is achieved, the rotary solenoid 24 to be actuated in the occasion of measurement is driven by sending a trigger signal from the computer 50 to the driving circuit 58.

On the occasion of tonometry, in order to form the image of the eye E on the image pickup element 37 of the viewing optical system of the tonometry unit 1, an examiner manipulates the track ball or the like with watching the display 48 to drive the lengthwise motion motor 5, the vertical motion motor 12, and/or the crosswise motion motor 18 to achieve alignment. At this time, the examinee is instructed to fix the sight at the fixed sight LED light source 46 from the tonometry unit 1 and the alignment optical system of the tonometry unit 1 is used to carry out accurate alignment of the tonometry unit 1 to the eye E to be examined.

Figure 6:
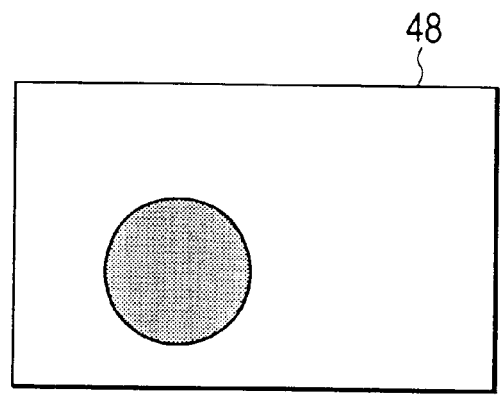
FIG. 6 is an explanatory diagram of detection of pupil.

When a key input to start auto-alignment is carried out in a state in which the pupil of the eye E is displayed more or less, the computer first determines whether the alignment brightness points are within a predetermined area of the image pickup element 37, based on the signal from the image pickup element. If they are not in the predetermined area, the computer performs such control that the driving circuit instantaneously increases the light amount of the anterior illuminating LED light sources 38a, 38b to near the maximum. The whole image at this time is taken into the image pickup element 37. The image thus taken in is one as illustrated in FIG. 6, in which the portion except for the pupil appears white, because a lot of reflected light of the light from the anterior illuminating LED light sources 38a, 38b is incident thereto, and in which the pupil part appears black, because no reflected light is incident thereto. Therefore, the computer 50 can extract the pupil part and determine the pupil position by detecting the contrast difference.

When the pupil position deviates from the appropriate alignment position, the computer computes an amount of the deviation and drives the vertical motion motor 12 and the crosswise motion motor 18 in accordance with the deviation amount so as to bring the pupil to the center. After alignment is made to some extent, the light received by the alignment optical system and the two alignment brightness points are received by the image pickup element 37 to be displayed on the display 48. When a positional deviation of the two alignment brightness points is detected based on the image pickup signal, the computer drives the lengthwise motion motor 5, the vertical motion motor 12, and/or the crosswise motion motor 18 so as to bring the system to the appropriate alignment position, i.e., so as to move the two brightness points onto the straight line and to the center. In this way, feedback control of auto-alignment is carried out, whereby the tonometry unit 1 can be automatically positioned at the appropriate alignment position.

Once the unit is positioned at the appropriate alignment position, a trigger signal is generated to automatically drive the airflow generator 22. The airflow generator 22 feeds air into the air chamber 23 and air is ejected from the nozzle 31 onto the cornea. The cornea is deformed by the blowing air and the output of the light receiving element 45 becomes pulsed in a predetermined deformation state of the cornea. At a peak of the pulse the pressure inside the air chamber 23 is measured by the pressure sensor 47 to be reduced to an intraocular tension value. This completes a series of operations from the alignment to the eye E to the tonometry.

Figure 7B:
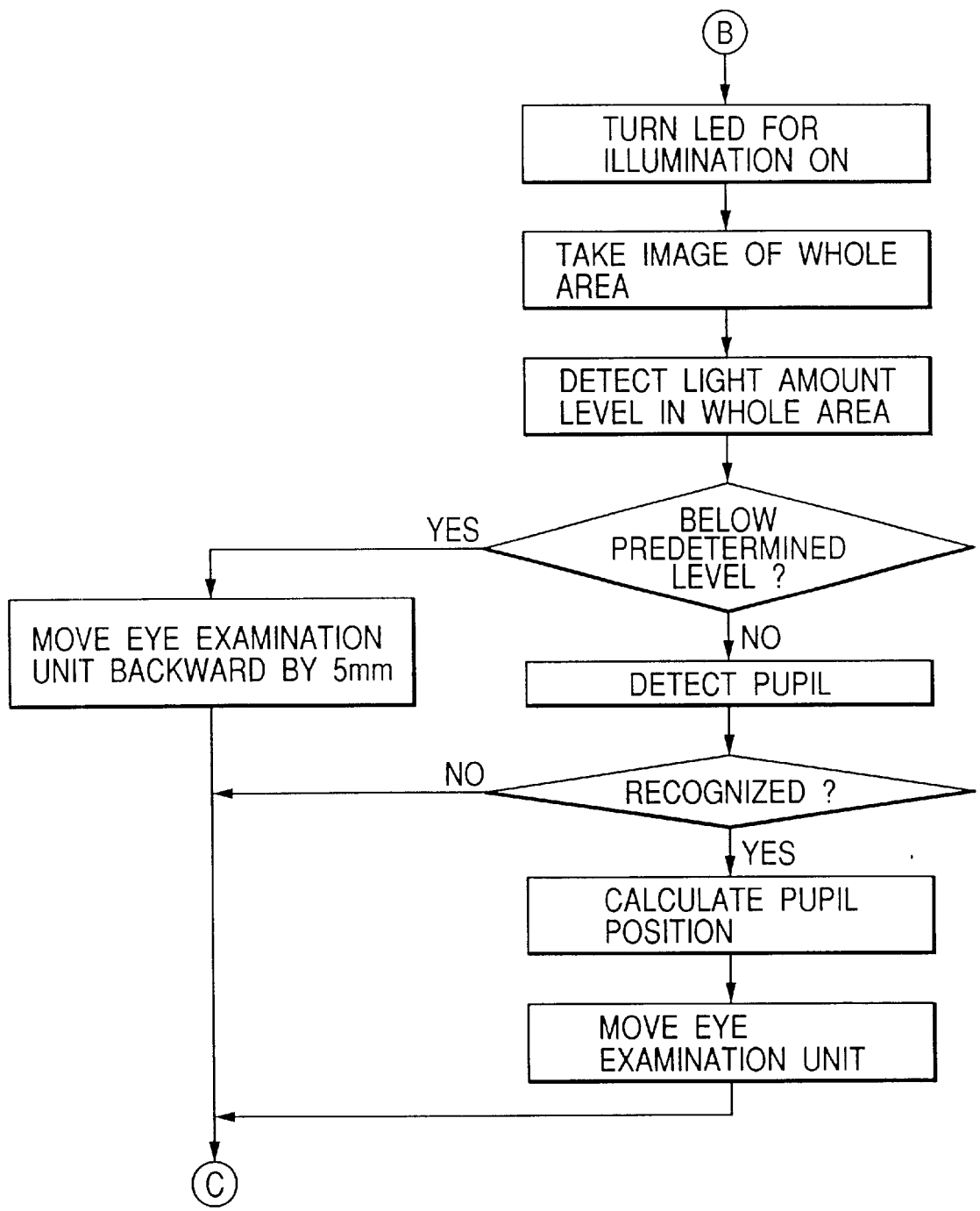
FIG. 7 is comprised of FIGS. 7A and 7B showing flowcharts of the first embodiment.

FIGS. 7A and 7B are flowcharts of the series of operational steps and processes A, B, C of FIGS. 7A and 7B represent three stages of processing procedures carried out for positioning by the computer. The process A is started with the key input for starting the auto-alignment to carry out a step of reading in an image of a predetermined area of the image pickup element 37 with the alignment brightness points thereon to find out whether the two alignment brightness points of the alignment detecting optical system can be detected. A next step is a recognition processing step to recognize the alignment brightness points. Once it is determined that they are recognized, the computer moves to a step of determining whether the alignment brightness points are at the appropriate position. If it is determined that the alignment brightness points are not recognized on the other hand, the computer transfers to the process B.

When in the step of determining whether the alignment brightness points are at the appropriate position it is determined that they are at the appropriate position, the computer moves to a process M of measurement control for tonometry. When it is determined that they are not at the appropriate position, the computer moves to a step of computing the brightness point positions. In that step, the computer computes X-directional and Y-directional positions of the center of gravity of the image pickup element 37 from information of size and brightness of the optical image of the brightness points displayed in the predetermined area and also computes how far they deviate from the appropriate alignment position. Further, the computer computes a driving amount to determine where the eye examination unit should be moved and then transfers to a step of driving the eye examination unit, based on the result of the computation, then going into the process C.

As described above, the alignment brightness points reflected by the cornea of the eye E are first looked for first in the process A, it is then determined with recognition thereof whether their positions are appropriate, and then the computer moves to the process M of tonometry if they are appropriate. Unless they are appropriate, the computer computes the amount of positional deviation to drive the driving unit. When the alignment brightness points cannot be recognized in the first stage, the computer transfers into the process B of detecting the pupil in a wider detection range of the eye E and taking the image of the whole area in instead of the predetermined area.

Figure 8:
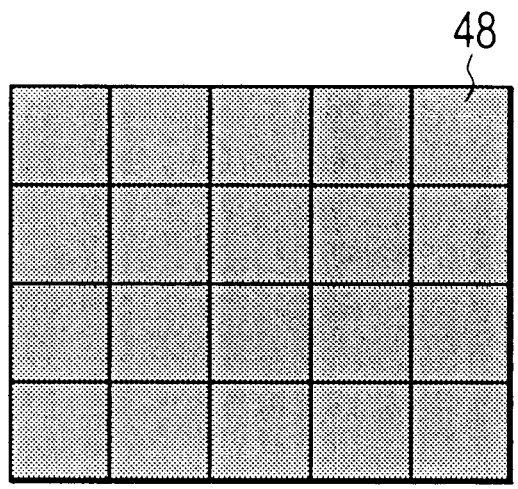
FIG. 8 is an explanatory diagram of a 20-divided image data display screen.
Figure 10:
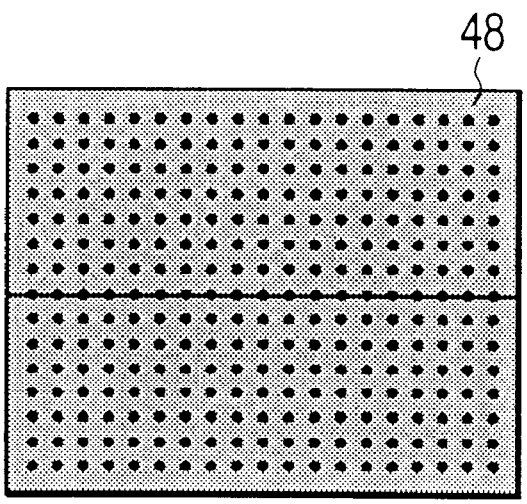
FIG. 10 is an explanatory diagram of a pixel-divided image data display screen.

First, the computer goes into an operational step of lighting the anterior illuminating LED light sources 38a, 38b at the maximum light amount in order to obtain a clearer image of the pupil of the eye E. After this lighting operation, a step of reading in the image of the whole area of the image pickup element 37 is carried out and after the capture of the image the light amount of the anterior illuminating LED light sources 38a, 38b is returned to the original amount. Then the flow goes to a step of detecting a light amount level at each pixel of the image data thus taken in the whole area. At this time, for example, when light amounts of the respective pixels are detected and if the maximum level of all the pixels is not more than a predetermined level, it can be determined that the whole area is dark. In another method, the whole area is divided into twenty areas in the image data thus taken as illustrated in FIG. 8 and it is determined that the whole area is dark, if an average light amount of the divided image data is not more than a predetermined level throughout the whole area. In a further method, typical pixels are set at equal intervals in the image data of the whole area as illustrated in FIG. 10 and it is determined that the whole area is dark, if light amounts of the typical pixels are not more than a predetermined level throughout the whole area.

Figure 9:
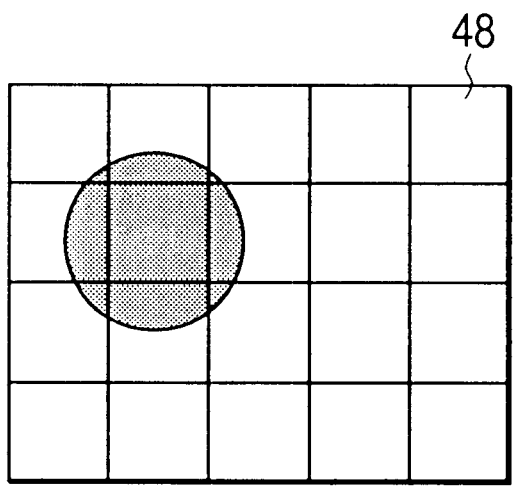
FIG. 9 is an explanatory diagram of detection of pupil.

When it is determined that the intensity is not more than the predetermined level by at least one of these determination methods, the computer carries out such an operation as to retract the eye examination unit by a predetermined distance, for example by 5 mm, in a direction away from the eye E and then transfers to the process C. On the other hand, if it is determined that a certain area is not less than the predetermined level, the computer goes into the process for detection of pupil to detect the pupil part from the image data of the whole area captured previously. For example, as shown in FIG. 9, the image data of nine adjacent areas are taken with respect to a reference at an area having the smallest average light amount of image data out of the twenty areas divided from the entire area and it is determined that the area represents the pupil, if the number of pixels having the light amounts of not more than the predetermined level is that equivalent to the average pupil area.

Figure 11:
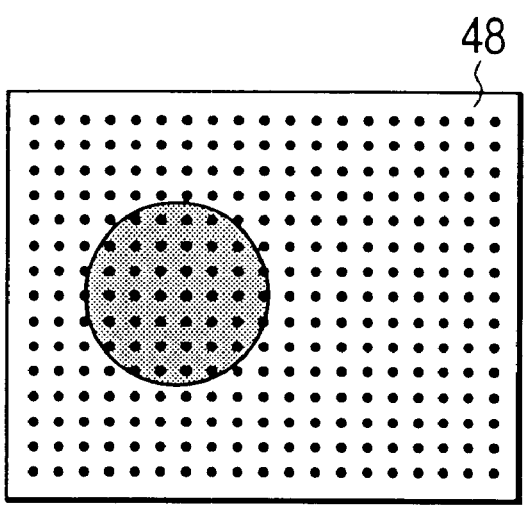
FIG. 11 is an explanatory diagram of detection of pupil.

In another method, if the total number of pixels, of which the typical pixels set at equal intervals in the image data of the whole area are not more than the predetermined level as illustrated in FIG. 11, is the number of pixels equivalent to the pupil area, it is determined that the area represents the pupil. When the pupil is discriminated in the determination step of recognizing it by these determination methods, the computer moves into a calculation step of calculating the position of the pupil. When it is determined that the pupil is not recognized, the computer transfers to the process C. In the calculation step of the position of pupil, a center of the area of the whole of the adjacent dark regions is calculated and is assumed to be a center position of the pupil. Further, when the apparatus is aligned with the eye E at the appropriate position, the center position of the pupil is assumed to be aligned with the center of the image pickup element 37 and the computer computes an amount of positional deviation of the computed pupil center position from the center of the image pickup element 37. A moving amount of the eye examination unit is computed based on this positional deviation amount and then the computer goes into an operational step of moving the eye examination unit, then transferring to the process C after the operational step.

The process C is a process carried out when the eye examination unit is moved to a limit position in the driving range or when the pupil of the eye E cannot be detected. When the operation goes into the process C after each step of operation, processing, or determination in the process A or B, the flow goes into a step of checking whether the limit sensor for indicating the limit position of the moving range of the eye examination unit is on. This sensor can be selected from optical detection type switches arranged so that a photointerrupter can pass between a light emitting unit and a light receiving unit, compact contact switches, and so on. When it is determined that the limit sensor is on, an alarm is given to the examiner by displaying a cancel indication to inform the examiner of cancellation of the auto-alignment operation on a view monitor or by a LED lamp or the like, or by giving a sound. Then the auto-alignment operation is ended and the eye examination unit is stopped at that position, thus terminating the series of operations.

On the other hand, when it is determined in the checking step of the limit sensor that the limit sensor is off, the flow goes into a step of counting the timer up. As the timer is counted up and when a predetermined time, for example ten seconds, has passed since triggering of auto-alignment start, the cancel indication to cancel the operation of auto-alignment is displayed in a similar fashion to the above and the series of operations are terminated. When the elapsed time after the counting-up is within ten seconds, the flow returns to the process A. Returning to the process A, the recognition of the alignment brightness points, the recognition of the pupil, etc. are carried out, and when the image data is not dark again without recognition of them, the timer is counted up.

As described above, the auto-alignment is discontinued after a lapse of the predetermined time, if the eye E cannot be detected; the auto-alignment is also discontinued after a lapse of the predetermined time, if the eye E moves though the eye E was recognized once; the auto-alignment is also discontinued at arrival at the limit of the moving range.

Figure 12:
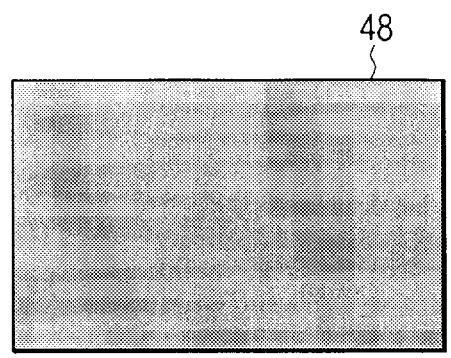
FIG. 12 is an explanatory diagram of a display screen in close proximity to the eye to be examined.

Since the tonometry unit 1 is automatically positioned during the auto-alignment, the examiner does not have to carry out anything up to the end of measurement unless the examiner forces the system to suspend the operation. However, if the eye E goes into close proximity to the tonometry unit 1 for some reason during the auto-alignment, there is a possibility that the unit touches the eye E with missing the detecting position because of a sudden positional change of the eye e. For this reason, the illumination range of the anterior illuminating LED light sources 38a, 38b is limited as illustrated in FIG. 2, and in the region S where the eye E is proximate to the tip of the nozzle 31, the entire observation range is covered so as to make the whole image receiving surface dark as illustrated in FIG. 12 by the shadow of lens barrel of lens 30, even if the anterior illuminating LED light sources 38a, 38b light bright.

When this darkening phenomenon is captured by the image pickup element 37, the tonometry unit 1 is retracted backward by several mm. For example, after the tonometry unit 1 is retracted backward by 5 mm and when the pupil part of the eye E and the alignment brightness points are extracted again, the auto-alignment is continued and tonometry is carried out. In this way the tonometry can be carried out safely, even if the eye E to be examined suddenly goes into close proximity to the apparatus during the auto-alignment. In the present embodiment the apparatus can be constructed so as to move back and forth, based on only the true observed image signal of the anterior part, without projection of a target toward the eye E.

Figure 13:
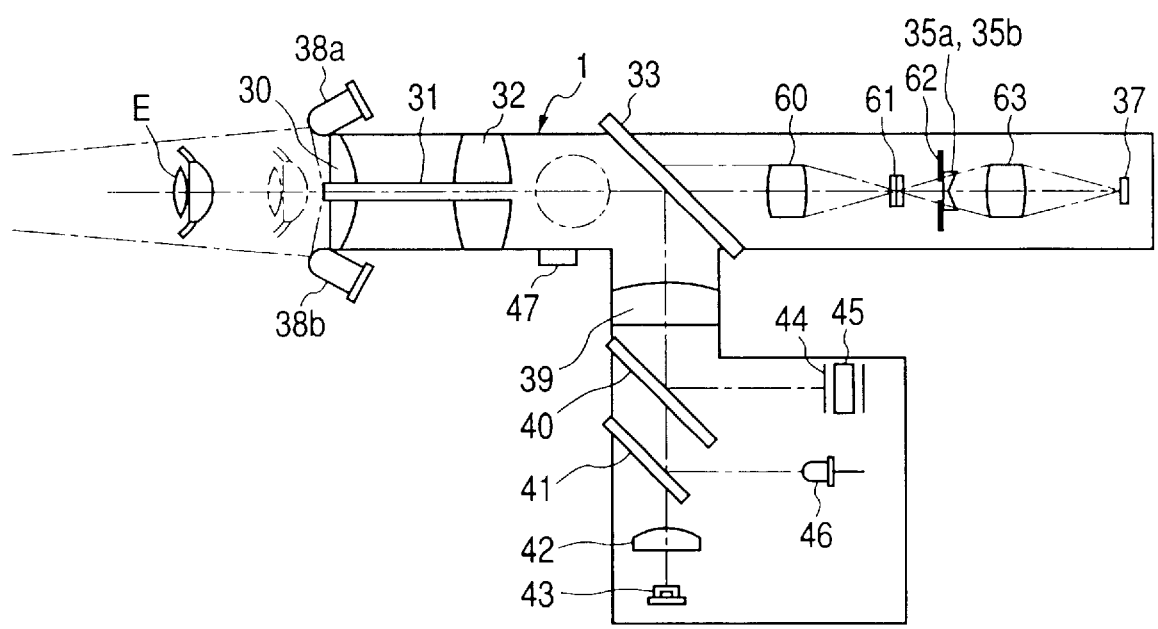
FIG. 13 is a side view of an optical system in the second embodiment.

FIG. 13 is a structural diagram of a tonometer of the second embodiment, in which the same reference symbols as those in the first embodiment denote the same members. The anterior illuminating LED light sources 38a, 38b are positioned adjacent to the lens 30, so as to always illuminate the eye E to be examined even in a close proximity state of the eye E to the tonometry unit 1. Behind the dichroic mirror 33 of the viewing optical system, there are a lens 60, a prism 61, a mask 62, and a lens 63 arranged in the stated order, and the image pickup element 37 is placed behind them. The mask 62 is provided with three apertures vertically aligned, similar to those in FIG. 3 though the orientation of the apertures is different; the center aperture is a little larger than the others in order to allow the light of the viewing optical system to pass therethrough, and the two apertures up and down are provided each with a filter for transmitting only the wavelength of the light source 43 as an alignment light source, and the separating prism 35a, 35b. Since the mask 62 is slightly shifted to the prism 61 side from the eye-E-side focal point of the lens 63, the image formed becomes larger but unsharper as the eye examination unit becomes more proximate to the eye E to be examined.

The viewing light from the anterior illuminating light sources 38a, 38b for observing the eye E to be examined travels through the lenses 30, 32 and the dichroic mirror 33 and then through the lens 60 to form an image in the prism 61. The light is refracted and separated in lateral directions opposite to each other by the upper half and the lower half of the prism 61. When the distance between the eye E and the tonometry unit 1 is longer than the appropriate working distance, the lens 60 focuses the viewing light at the image position closer to the lens 60 than the prism 61 and the observed image is formed with the upper half being shifted to the right and with the lower half being shifted to the left. On the other hand, when the distance between the eye E and the tonometry unit 1 is shorter than the appropriate working distance, the image is formed closer to the lens 63 than the prism 61 and the observed image is formed with the upper half being shifted to the left and with the lower half being shifted to the right.

Figure 14:
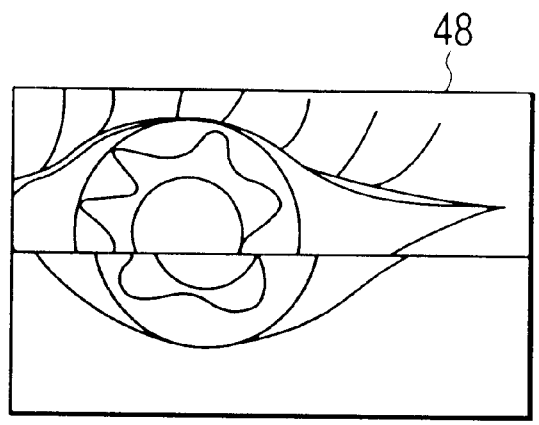
FIG. 14 is an explanatory diagram of an observed image in a shifted state.
Figure 15:
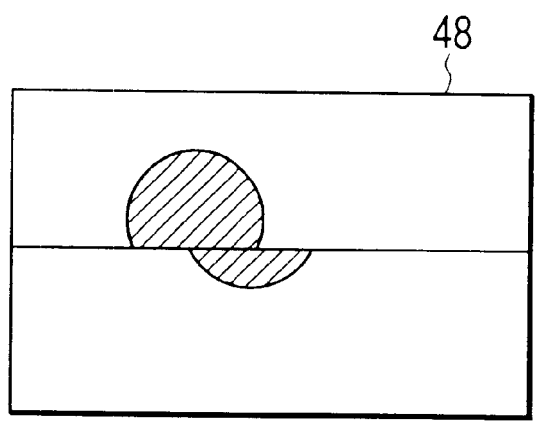
FIG. 15 is an explanatory diagram of detection of pupil.

FIG. 14 shows an image on the display 48 obtained when the eye E is in close proximity to the tonometry unit 1 and in a slightly leftwardly shifted state. FIG. 15 shows an image of the pupil detected when the eye E becomes proximate to the tonometry unit 1 during the auto-alignment, and this pupil image is stored in the image memory 52. Each of the two pupil images separated up and down is considered to be a part of a circle and their center positions are obtained. When a lateral shift amount between the center positions of the two partial circles is greater than a predetermined value, it is determined that the eye E to be examined is abnormally proximate to the tonometry unit 1. When the whole pupil is imaged in only either one of the upper half and the lower half and if the size of the pupil is greater than a predetermined value, it is also determined that the eye E is abnormally proximate to the unit.

Further, if the lateral shift amount between the center positions of the two partial circles or the size of the pupil is not more than the predetermined value, alignment deviation is judged; vertical and lateral positional deviation of the eye E is discriminated based on the deviation of the position of the whole pupil from the center of the image pickup surface. Since the abnormal proximity and alignment deviation can be detected by detection of the pupil as described above, the computer controls the lengthwise motion motor 5, the vertical motion motor 12, and the crosswise motion motor 18 through the driving circuit 57 so as to move the unit to the appropriate alignment position.

The conventional alignment optical systems using the cornea-reflected light cannot receive the cornea-reflected light unless the viewing optical axis is accurately aligned with the vertex of cornea, whereas the viewing optical system of the present embodiment can detect the position of pupil within the range in which the pupil of the eye E can be observed. Therefore, the present embodiment permits the detection of auto-alignment based on the detection of position in the wide range, thus improving operability.

Figure 16:
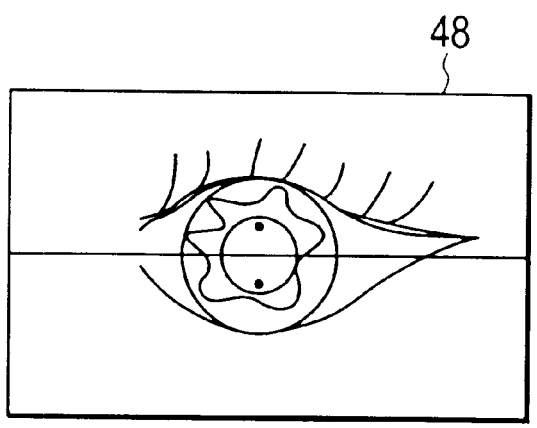
FIG. 16 is an explanatory diagram of an observed image in an aligned state.

Just as being the case in the first embodiment, the cornea-reflected light of the alignment detecting optical system travels through the separating prisms 35a, 35b on the mask 62 and through the lens 63 to form the alignment spots on the image pickup element 37, so that in the present embodiment the alignment brightness points appear in combination with the anterior-observed image in the observed image separated by the prism 60, on the display 48, as illustrated in FIG. 16. In this way the alignment detection can be carried out more accurately with the alignment brightness points and a detection error can be prevented.

FIGS. 17A and 17B are flowcharts of a series of operational steps. In the process A, similar to that in the first embodiment, it is first determined whether the alignment brightness points of the cornea-reflected image of the eye E can be recognized and the flow goes to the process B, if they cannot be recognized. If the brightness points are recognized and if their positions are appropriate, the flow moves to the step of tonometry. If the brightness points are recognized but if their positions are not appropriate, the operational step of moving the eye examination unit to the appropriate position is carried out.

In the process B, the pupil is detected in the wider detection range of the eye E and various processes and determinations are carried out using the image data captured from the image of the whole area instead of the predetermined area. First, in order to obtain a clearer image of the pupil of the eye E, the computer goes into the operational step of lighting the anterior illuminating LED light sources 38a, 38b at the maximum light amount. After this lighting operation, the computer carries out the step of reading in the image from the whole area of the image pickup element 37. Further, the flow moves to the processing step of detecting the pupil, based on the thus captured image data of the whole area. After the data is taken in, the light amount of the anterior illuminating LED light sources 38a, 38b is returned to the original light amount.

Figure 18:
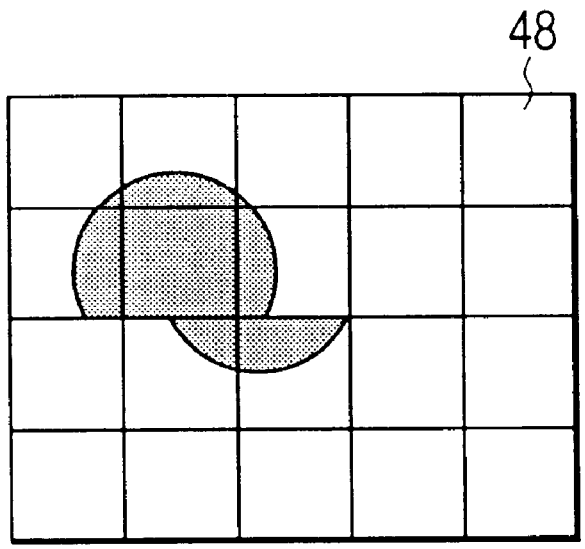
FIG. 18 is an explanatory diagram of detection of pupil.
Figure 19:
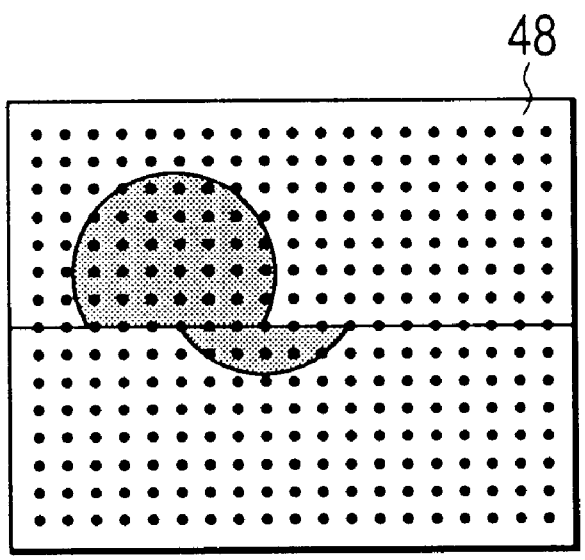
FIG. 19 is an explanatory diagram of detection of pupil.

For example, as illustrated in FIG. 18, the whole area is divided into the upper half and the lower half by the separating prisms, each half is divided into ten segmental areas, and image data of six adjacent areas are taken in with respect to a reference at an area having a smallest average light amount in the image data of the upper half and the lower half separated. The sum is computed of pixels whose light amount is not more than the predetermined level in the upper half and the lower half and it is determined that the image represents the pupil, if the number of pixels is that equivalent to the average pupil area. In another method, as illustrated in FIG. 19, the number of pixels below the predetermined level is counted out of the typical pixels set at equal intervals in the image data of the whole area and it is determined that the image represents the pupil, if the total number of pixels is that equivalent to the pupil area.

Once the pupil is recognized in the determination step of recognizing it, the computer goes into a determination step of determining whether the pupil is split. If the pupil is not recognized the flow goes into the process C. It is determined whether the pupil recognized is split on the image pickup element 37 by the separating prisms 35a, 35b and lies across the boundary between the upper half and the lower half. When the pupil is discriminated, center positions of the pupil images in the upper half and in the lower half are computed each from a boundary arc between the pupil and the iris, i.e., from a boundary arc between pixels of the black level and pixels of the white level. When it is determined that the pupil does not lie across the border, the flow goes into the determination step of determining whether the size of the pupil in the upper half or in the lower half is not less than the predetermined value.

In the pupil position calculation step of calculating the pupil center position of each of the upper half and the lower half from the boundary arc between the pupil and the iris, a lengthwise positional deviation can be detected from vertical and crosswise positional deviations from the center of the image pickup element 37 and X-directional difference and sign between the upper half and the lower half. After calculating a moving amount of the eye examination unit, the computer goes into the operational step of moving the eye examination unit. The size of the pupil can be determined from the number of pixels in the image recognized as the pupil previously and it is determined whether the X-directional difference between the pupil centers of the upper half and the lower half is not less than a predetermined value. If it is not less than the predetermined value, the eye examination unit is retracted backward by a predetermined distance, for example by 5 mm, in the direction away from the eye E and then the flow goes into the process C. On the other hand, if it is determined that the X-directional difference is below the predetermined value, then the computer carries out a pupil position calculating step of calculating pupil center positions of the upper half and the lower half and calculating their deviation from the center of the image pickup element 37. Then the flow goes into the operational step of calculating a moving amount of the eye examination unit and thereafter moving the eye examination unit, and thereafter moves into the process C after the movement of the eye examination unit.

The process C is a process carried out when the eye examination unit is moved to the limit position of the driving range or when the pupil of the eye E cannot be detected, which is similar to FIGS. 7A and 7B, and thus the description thereof is omitted herein.

Figure 20:
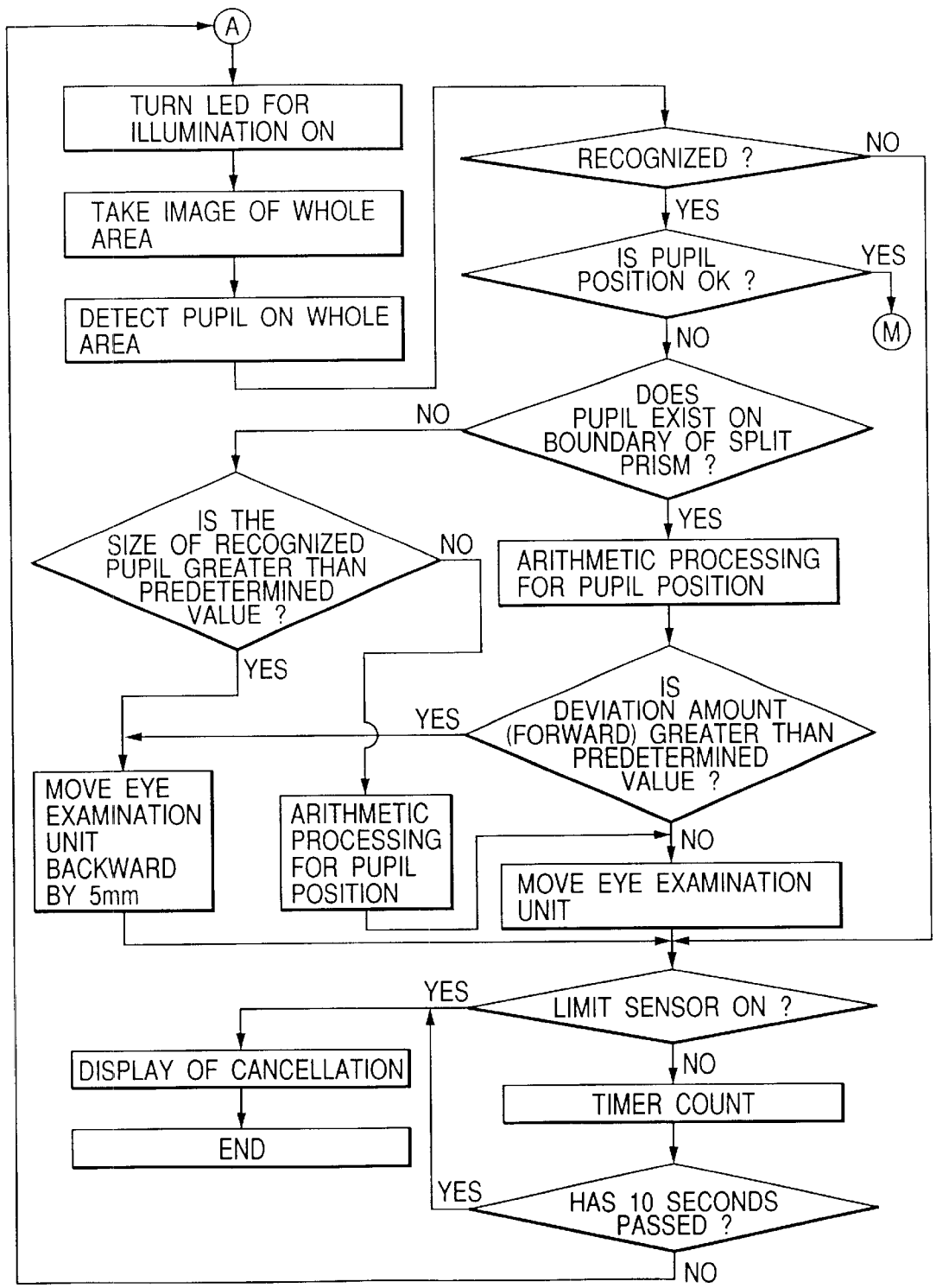
FIG. 20 is a flowchart of the third embodiment.

The above embodiment employed the algorithm of measurement to carry out the more accurate alignment by use of the alignment brightness points of the cornea-reflected image of the eye E, whereas FIG. 20 shows a flowchart for eye examination wherein measurement is carried out based on the alignment by only the detection of pupil. In this flowchart of FIG. 20 the processes B and C in FIGS. 17A and 17B are combined, and a pupil position determining step of determining whether alignment between the eye E and the eye examination unit is within an appropriate range, based on the pupil position, is added after the determination step of recognizing the pupil. Once it is determined that alignment is within the appropriate range, the flow goes into the eye examination step; if it is outside the appropriate range, the flow goes into the determination step of determining whether the pupil lies across the border formed by the separating prisms 35a, 35b, similar to the process B of FIGS. 17A and 17B. When the pupil is detected only in either one of the upper half and the lower half split by the separating prisms 35a, 35b, the pupil is once aligned with the center position at the border, and then the lengthwise positional deviation of the eye examination unit to the eye E can be detected.

In the case of the apparatus in which the driving unit is limited so as to avoid proximity over a predetermined distance according to the eye E before measurement, where the preset distance is close to the appropriate alignment position, the measurement could be suspended because of the limit during the auto-alignment. In contrast with it, the present embodiment can be arranged to revise the set limit distance with a higher priority to the position of the eye E during the auto-alignment, even if the eye E gradually approaches the apparatus from the preset position and then leaves.

The present invention can also be applied to other ophthalmic apparatuses such as fundus cameras, refractometers, or the like, as well as the tonometers.

As described above, the ophthalmic apparatus according to the present invention can detect the position of the eye E in the wide range by the relatively simple structure to detect the position of the eye E using the observed image signal of the eye examination unit and control the eye examination unit in the lengthwise directions, based on this positional information; therefore, it effectively works to carry out the auto-alignment and anti-proximity, and the operability and safety for examinee can be improved.

The ophthalmic apparatus according to the present invention can also detect the position of the eye E in the wide range by the relatively simple structure to detect the amount and direction of image deviation of the pupil image by the prisms and control the eye examination unit in the lengthwise directions, based on the deviation amount and direction information; therefore, it effectively works to carry out the auto-alignment and anti-proximity, and the operability and safety for examinee can be improved.

Further, the ophthalmic apparatus according to the present invention can also detect the position of the eye E in the wide range by the relatively simple structure to recognize the pupil of the eye from the observed image, detect the size of the pupil image, and control the eye examination unit in the lengthwise directions, based on this size information; therefore, it effectively works to carry out the auto-alignment and anti-proximity, and the operability and safety for examinee can be improved.

What is claimed is:

1. An ophthalmic apparatus comprising:
   a measurement unit for measuring an eye to be examined;
   an illumination light source disposed near the measurement unit, for illuminating the eye;
   an area sensor for picking up an image of the eye illuminated by said illumination light source;
   driving means for driving said measurement unit relative to the eye forward or backward;
   determining means for determining whether signal levels throughout an entire area of said area sensor are not more than a predetermined level; and
   control means for controlling said driving means so as to drive the measurement unit away from said eye, when said determining means determines that the signal levels are not more than the predetermined level.

2. The apparatus according to claim 1, wherein said area sensor is located at a conjugate position with the anterior part of the eye.

3. The apparatus according to claim 1, further comprising an irradiation light source for irradiating measurement light to the anterior part of the eye, wherein a plurality of cornea-reflected images of the light from the irradiation light source are projected onto said area sensor.

4. The apparatus according to claim 3, further comprising light amount control means for increasing a light amount of said illumination light source when said determining means determines that the signal levels are not less than the predetermined level and when said cornea-reflected images are not detected based on an output of said area sensor.

5. The apparatus according to claim 3, further comprising pupil detecting means for detecting a position of the pupil part of the eye, based on an output of said area sensor, when said determining means determines that the signal levels are not less than the predetermined level, wherein said driving means is able to drive said measurement unit left and right and up and down, and wherein said drive control means drives said driving means, based on the position of the pupil detected by said pupil detecting means.

6. The apparatus according to claim 3, further comprising cornea detecting means for detecting positions of said plurality of cornea-reflected images, based on the output of said area sensor, wherein said driving means is able to drive said measurement unit left and right and up and down, and wherein said drive control means drives said driving means, based on the positions of the cornea detected by said cornea detecting means.

7. An ophthalmic apparatus comprising:
   a measurement unit for measuring an eye to be examined;
   an illumination light source disposed near the measurement unit, for illuminating the eye;
   an area sensor for picking up an image of the anterior part of the eye illuminated by said illumination light source;
   an optical unit for optically splitting the image of the anterior part and for projecting the images of the anterior part thus split onto said area sensor;
   driving means for driving said measurement unit relative to the eye forward or backward;
   detecting means for detecting a deviation amount between the images of the pupil split by said optical unit, based on an output of said area sensor; and
   control means for controlling said driving means so as to drive the measurement unit away from said eye, based on the result of detection by said detecting means.

8. The apparatus according to claim 7, wherein said control means controls said driving means so as to drive the measurement unit away from said eye when said detecting means determines that the deviation amount of the pupil is not less than a predetermined value.

9. The apparatus according to claim 8, wherein said detecting means further detects a direction of the deviation between the images of the pupil and wherein when said determining means determines that the deviation amount of the pupil is not more than the predetermined value, said control means controls said driving means so as to drive the measurement unit in a direction according to the direction of said deviation determined by said determining means.

10. An ophthalmic apparatus comprising:
    a measurement unit for measuring an eye to be examined;
    an illumination light source disposed near the measurement unit, for illuminating the eye;
    an area sensor for picking up an image of the anterior part of the eye illuminated by said illumination light source;
    driving means for driving said measurement unit relative to the eye forward or backward;
    determining means for determining a size of the pupil of the eye, based on an output of said area sensor; and
    control means for controlling said driving means so as to drive the measurement unit away from said eye, based on the result of determination by said determining means.

11. The apparatus according to claim 10, wherein when said determining means determines that the size of the pupil is not less than a predetermined value, said control means controls said driving means so as to drive the measurement unit away from said eye.

12. An ophthalmic apparatus comprising:
    a measurement unit for measuring an eye to be examined;
    an area sensor for picking up an image of the eye;
    driving means for driving said measurement unit relative to the eye forward or backward;
    determining means for determining whether signal levels at a predetermined area of said area sensor not more than a predetermined level; and control means for controlling said driving means such that the measurement unit is driven so as not to approach further to said eye, when said determining means determines that the signal levels are not more than the predetermined level.

13. An ophthalmic apparatus comprising:

a measurement unit for measuring an eye to be examined;

an area sensor for picking up an image of the anterior part of the eye;

an optical unit for optically splitting the image of the anterior part and for projecting the image of the anterior part thus split onto said area sensor;

driving means for driving said measurement unit relative to the eye forward or backward;

detecting means for detecting a deviation amount between the images of the anterior part split by said optical unit based on an output of said area sensor; and control means for controlling said driving means such that the measurement unit is driven so as not to approach further to said eye based on the result of detection by said detecting means.

14. An ophthalmic apparatus comprising:

a measurement unit for measuring an eye to be examined;

an area sensor for picking up an image of the anterior part of the eye;

driving means for driving said measurement unit relative to the eye forward or backward;

determining means for determining a size of the image of the eye based on an output of said area sensor; and control means for controlling said driving means such that the measurement unit is driven so as not to approach further to said eye based on the result of determination by said determining means.

* * * * *

UNITED STATES PATENT AND TRADEMARK OFFICE
CERTIFICATE OF CORRECTION

PATENT NO. : 6,409,343 B1
DATED : June 25, 2002
INVENTOR(S) : Koji Uchida

It is certified that error appears in the above-identified patent and that said Letters Patent is hereby corrected as shown below:

Column 9,
Line 32, after "eye" delete "e." and insert -- E. --.

Signed and Sealed this

Eleventh Day of March, 2003

JAMES E. ROGAN
*Director of the United States Patent and Trademark Office*